United States Patent
Granier et al.

(10) Patent No.: US 7,605,118 B2
(45) Date of Patent: Oct. 20, 2009

(54) CYCLOOCT-(EN-)YL DERIVATIVES FOR USE AS FRAGRANCES

(75) Inventors: Thierry Granier, Dubendorf (CH); Jerzy A. Bajgrowicz, Zurich (CH); Andreas Hanhart, Uster (CH)

(73) Assignee: Givaudan SA, Vernier (CH)

( * ) Notice: Subject to any disclaimer, the term of this patent is extended or adjusted under 35 U.S.C. 154(b) by 621 days.

(21) Appl. No.: 10/531,809

(22) PCT Filed: Oct. 8, 2003

(86) PCT No.: PCT/CH03/00660

§ 371 (c)(1), (2), (4) Date: Apr. 18, 2005

(87) PCT Pub. No.: WO2004/035017

PCT Pub. Date: Apr. 29, 2004

(65) Prior Publication Data

US 2006/0014663 A1    Jan. 19, 2006

(30) Foreign Application Priority Data

Oct. 21, 2002 (GB) ................ 0224379.8
Aug. 19, 2003 (GB) ................ 0319350.5

(51) Int. Cl.
*A61K 8/00* (2006.01)

(52) U.S. Cl. ............... 512/1; 512/27; 424/59

(58) Field of Classification Search ........ 512/1
See application file for complete search history.

(56) References Cited

U.S. PATENT DOCUMENTS

| 4,152,366 | A | * | 5/1979 | Wilke et al. .......... 585/16 |
| 4,214,098 | A |   | 7/1980 | De Jong et al. ....... 560/231 |
| 4,255,595 | A | * | 3/1981 | Wilke et al. .......... 568/821 |
| 6,252,118 | B1 | * | 6/2001 | Jun et al. ............ 568/317 |
| 6,555,517 | B1 |   | 4/2003 | Markert et al. ....... 512/27 |
| 6,869,598 | B2 | * | 3/2005 | Love et al. .......... 424/59 |

FOREIGN PATENT DOCUMENTS

| DE | 36 10 049 A | 10/1986 |
| DE | 19814913 A1 | 10/1999 |
| WO | WO 99 51713 A | 10/1999 |

OTHER PUBLICATIONS

Freerksen, Robert W. et al., Journal of Organic Chemistry, 1982, vol. 48, pp. 4087-4096.*
Bajgrowicz, Jerzy A. et al., Bioorganic and Medicinal Chemistry 11, 2003, pp. 2931-2946.*
Dixon J.R., et al.: "Mass Spectral Data of Cyclooctyl Derivatives"; Journal of Chemical and Engineering Data, vol. 20, No. 1, pp. 123-124; XP001157123; the whole document.
Journal of Organic Chemistry, 1971, vol. 36(5), pp. 670-676, see compound 5 (p. 671).
International Search Report dated Jan. 12, 2004 for Application PCT/CH03/00660.
Search Report from The Patent Office in Great Britain dated Mar. 18, 2003 for Application GB 0224379.8.

* cited by examiner

*Primary Examiner*—Mark Eashoo
*Assistant Examiner*—Thuy-ai N Nguyen
(74) *Attorney, Agent, or Firm*—Norris McLaughlin & Marcus, P.A.

(57) ABSTRACT

This invention relates to substituted cyclooctenes of the formula I, wherein X and R are defined in the specification.

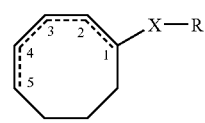

5 Claims, No Drawings

CYCLOOCT-(EN-)YL DERIVATIVES FOR USE AS FRAGRANCES

This invention relates to substituted cyclooctenes having agrestic, natural, and floral, green, woody odour notes, their manufacture, and to fragrance compositions containing them.

Substituted cyclooctenes have been described in the literature, for example, the German patent publication DE 19814913 A1 discloses cyclooctene aldehydes, such as cyclooct-4-en aldehyde (1) possessing an odour note described to be comparable with the odour of fresh harvested potatoes.

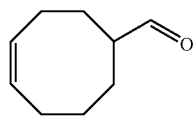 (1)

Whereas the odour notes imparted by cyclooct-4-en aldehyde (1) may be interesting in their own right, in the fragrance industry, there is always an ongoing demand for new compounds that enhance or improve on odour notes, or impart new odour notes.

Surprisingly, we have now found certain monosubstituted cyclooctenes structurally similar to (1), but which possess characteristically different odour notes which are described as agrestic and thujone-like, and floral, green, woody odour notes.

In a first aspect, the invention refers to the use of a compound of formula I as fragrance,

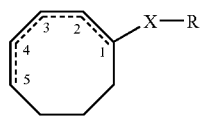 I wherein X is carbonyl, or —(CHOH)—; and

R is methyl or ethyl, or linear or branched $C_3$ to $C_5$ alkyl, such as i-propyl, n-propyl, n-butyl, sec-butyl, tert-butyl, n-pentyl, sec-pentyl, and tert-pentyl; or R is vinyl, or linear or branched $C_3$ to $C_5$ alkenyl, such as propen-1-yl, propen-2-yl, allyl, but-1-en-1-yl, but-2-en-1-yl, but-3-en-1-yl, and pentenyl; and the dotted line represents one optional double bond.

The compounds according to the present invention may contain one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective syntheses.

Preferred compounds of formula I are 1-cyclooct-3-enylethanone, 1-cyclooct-3-enylpropan-1-one, 1-cyclooct-3-enyl-2-methylpropan-1-one, 1-cyclooct-3-enylpropan-1-ol, 1-cyclooct-4-enylethanone, 1-cyclooct-2-enylethanone, 1-cyclooct-2-enylethanol, 1-cyclooct-1-enylethanone, 1-cyclooctylpropanone, 1-cyclooctyl-2-methylpropanone, and 1-cyclooctyl-2-methylpropanol.

Particularly preferred are compounds of formula I having a double bond at position C-3, i.e. a compound of formula I wherein the bond between C-3 and C-4 together with the dotted line represents a double bond, and the bonds between C-1 and C-2, C-2 and C-3, and C-4 and C-5 represent each a single bond, such as 1-cyclooct-3-enylethanone, 1-cyclooct-3-enylpropan-1-one, 1-cyclooct-3-enyl-2-methylpropan-1-one and 1-cyclooct-3-enylpropan-1-ol.

As used in relation to compounds of formula I "one optional double bond" refers to compounds of formula I wherein the bond between C-1 and C-2 together with the dotted line represents a double bond, and the bonds between C-2 and C-3, C-3 and C-4, and C-4 and C-5 represent each a single bond; or the bond between C-2 and C-3 together with the dotted line represents a double bond, and the bonds between C-1 and C-2, C-3 and C-4, and C-4 and C-5 represent each a single bond; or the bond between C-3 and C-4 together with the dotted line represents a double bond, and the bonds between C-1 and C-2, C-2 and C-3, and C-4 and C-5 represent each a single bond; or the bond between C-4 and C-5 together with the dotted line represents a double bond, and the bonds between C-1 and C-2, C-2 and C-3, and C-3 and C-4 represent each a single bond; or the bonds between C-1 and C-2, C-2 and C-3, C-3 and C-4, and C-4 and C-5 represent each a single bond.

The compounds according to the present invention may be used alone or in combination with known odourant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

The following list comprises examples of known odourant molecules, which may be combined with the compounds of the present invention:

natural products: tree moss absolute, basil oil, tropical fruit oils (such as bergamot oil, mandarin oil, etc.), mastix absolute, myrtle oil, palmarosa oil, patchouli oil, petitgrain oil, wormwood oil, lavender oil, rose oil, jasmin oil, ylang-ylang oil.

alcohols: farnesol, geraniol, linalool, nerol, phenylethyl alcohol, rhodinol, cinnamic alcohol, (Z)-hex-3-en-1-ol, menthol, α-terpineol.

aldehydes: citral, α-hexyl cinnamaldehyde, Lilial, methylionone, verbenone, nootkatone, geranylacetone.

esters: allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate.

lactones: γ-undecalactone, δ-decalactone, pentadecanolide, 12-oxahexadecanolide.

acetals: Viridine (phenylacetaldehyde dimethylacetal).

other components often used in perfumery: indole, p-mentha-8-thiol-3-one, methyleugenol, eugenol, anethol.

Whereas a single compound of formula I enhances, or improves on odour notes in their own right, it was found that a mixture of double bond isomers enhances the diffusion of a fragrance even more. Thus, the present invention refers in a further aspect to a fragrance composition comprising a mixture of A) a compound of formula Ic; and B) at least one compound selected from a compound of formula Ia, a compound of formula Ib, and a compound of formula Id

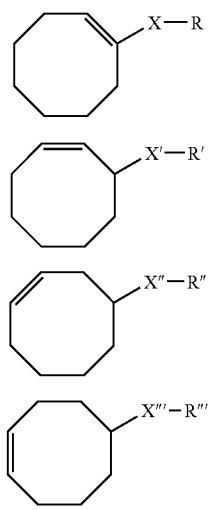

wherein X and R have the same meaning as defined above and R=R'=R"=R'" and X=X'=X"=X'".

Particularly preferred are mixtures comprising a compound of formula Ia, a compound of formula Ic, and a compound of formula Id. Preferred mixtures are those comprising at least 50% by weight of a compound of formula Ic based on the total weight of all double bond isomers, i.e. amount of the compound of formula Ia+Ib+Ic+Id=100% by weight.

The compounds of the present invention may be used in a broad range of fragrance applications, e.g. in any field of fine and functional perfumery. The compounds can be employed in wide ranging amounts depending upon the specific application and on the nature and quantity of other odourant ingredients, that may be for example, from about 0.001 to about 20 weight percent of the application. In one embodiment, compounds may be employed in a fabric softener in an amount of about 0.001 to 0.05 weight percent. In another embodiment, compounds of the present invention may be used in an alcoholic solution in amounts of about 0.1 to 20 weight percent, more preferably between about 0.1 and 5 weight percent. However, these values should not be regarded as limiting the present invention, since the experienced perfumer may also achieve effects or may create novel accords with lower or higher concentrations.

The compounds of the present invention may be employed into the fragrance application simply by direct mixing the compound of the present invention or the fragrance composition comprising the compound with the fragrance application. Alternatively, they may be added in an entrapped form, by being in a previous step entrapped with an entrapment material, for example polymers, capsules, microcapsules and nanocapsules, liposomes, precursors, film formers, absorbents, for example by using carbon or zeolites, cyclic oligosaccharides and mixtures thereof, and then mixed with the application.

Thus, the invention additionally provides a method of manufacturing a fragrance application, comprising the incorporation of a compound of formula I as a fragrance ingredient, either by directly admixing the compound of formula I into the application or by admixing a fragrance composition comprising a compound of formula I, which may then be mixed to a fragrance application, using conventional techniques and methods.

As used herein, "fragrance application" means any product, such as fine perfumery, e.g. perfume and Eau de Toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

Whereas some compounds have been described in the literature, others have not, and are novel. Thus, in another aspect of the invention, there is provided a compound of formula I

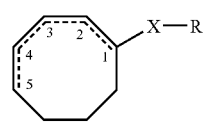

wherein X is carbonyl, or —(CHOH)—; and

R is methyl or ethyl, or linear or branched $C_3$ to $C_5$ alkyl, such as i-propyl, n-propyl, n-butyl, sec-butyl, tert-butyl, n-pentyl, sec-pentyl, and tert-pentyl; or R is vinyl or linear or branched $C_3$ to $C_5$ alkenyl, such as propen-1-yl, propen-2-yl, allyl, but-1-en-1-yl, but-2-en-1-yl, but-3-en-1-yl, and pentenyl; and the dotted line represents one optional double bond;

provided that when X is carbonyl and one of the bonds between C-1 and C-2, C-2 and C-3, and C-3 and C-4 together with the dotted line is a double bond, R is not methyl or ethyl;

when X is carbonyl and the bond between C-2 and C-3 together with the dotted line is a double bond, R is not i-propyl;

when X is carbonyl and the bond between C-3 and C-4 together with the dotted line is a double bond, R is not methyl or ethyl;

when X is carbonyl and all of the bonds between C-1 and C-2, C-2 and C-3, C-3 and C-4, and C-4 and C-5 together with the dotted line represent each a single bond, R is not methyl or ethyl;

when X is —(CHOH)—, R is not methyl; and when X is —(CHOH)— and the bond between C-2 and C-3 together with the dotted line is a double bond, R is not ethyl.

Compounds of formula I, wherein the bond between C-3 and C-4 together with the dotted line represents a double bond, i.e. substituted cyclooct-3-enes, may be prepared by the reaction of olefins with an appropriately substituted carboxylic acid, well known to a person skilled in the art and described for example by Schellhammer (Methoden der Organischen Chemie (Houben-Weyl), 1973, Band VII/2a, pages 447 -460) herein incorporated by reference, starting from cyclooctene by acylation with the appropriately substituted carboxylic acid. The resulting ketones (2) may be reduced to give further compounds of formula I as shown in scheme 1.

Scheme1:

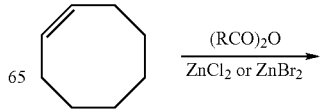

-continued

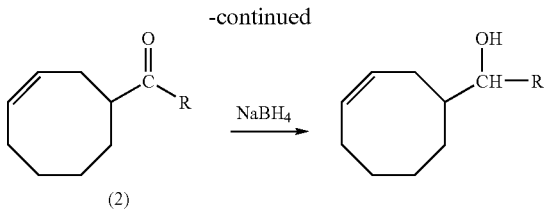

(2)

Compounds of formula I, wherein the bond between C-2 and C-3 together with the dotted line represents a double bond, i.e. substituted cyclooct-2-enes, may be prepared by selective bromination of cyclooctene, resulting in 3-bromocyclooctene, followed by addition of the appropriate aldehyde R—CHO under Grignard type reaction conditions known to the person skilled in the art. The resulting alcohols (3) may be oxidised to give further compounds of formula I as shown in scheme 2.

Scheme 2:

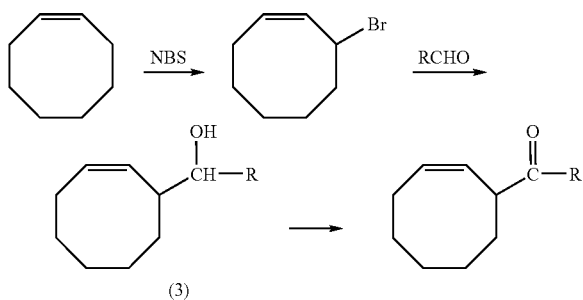

(3)

Compounds of formula I wherein the bond between C-4 and C-5 together with the dotted line represents a double bond, i.e. substituted cyclooct-4-enes, may be prepared by selective bromination under acidic conditions starting from cycloocta-1,5-diene, resulting in 5-bromo-cyclooctene, followed by addition of the appropriate aldehyde under Grignard conditions, resulting in an alcohol which may be oxidised to give further compounds of formula I.

Compounds of formula I wherein the bond between C-1 and C-2 together with the dotted line represents a double bond, i.e. substituted cyclooct-1-enes, may be prepared by the reaction of the appropriate alkynes with cyclooctanone under alkaline conditions, followed by Rupe rearrangement under acidic conditions.

Alternatively, a double bond isomeric mixture of compounds of formula I, i.e. a mixture of substituted cyclooct-1-enes, -3-enes and 4-enes, may be prepared by addition of an alkanoic acid chloride to cyclooctene followed by dehydrochlorination of the resulting chloro-cyclootyl alkanone under conditions known to the person skilled in the art.

Further particulars as to reaction conditions are provided in the examples.

There now follows a series of non-limiting examples that illustrate the invention.

EXAMPLE 1

1-cyclooct-3-enylethanone

To cyclooctene (300 g, 2.73 mol) were added acetic anhydride (556 g, 5.45 mol) and zinc chloride (30 g, 0.22 mol). The reaction mixture was warmed to 90-95° C. within 30 min., stirred at that temperature during 7.5 hours, cooled to 60° C., and treated with caution, within 10 min., with water (400 ml). The resulting mixture was heated at 100° C. during 3 h., cooled to 25° C., and extracted with hexane (3×300 ml). The combined organic phases were washed with aq. sat. NaCl soln. (800 ml), aq. sat. NaHCO$_3$ soln. (800 ml), aq. sat. NaCl soln. (400 ml), and dried (Na$_2$SO$_4$). Evaporation of the solvent led to 375 g of crude material which was distilled under vacuum with a short-path Vigreux column. After collecting the unreacted cyclooctene (65 g, 21.7%) at 40-50° C./100 mbar, the fractions distilling at 110° C./24 mbar were collected (144 g) and redistilled using a microdistillation column (20×1.5 cm, filled with 3×3 mm rolled wire netting) to give 110 g of 1-cyclooct-3-enylethanone (34% based on the reacted cyclooctene, 109° C./20 mbar) as colourless oil.

$^1$H-NMR (400 MHz, CDCl$_3$): δ1.40-1.85 (m, 6H), 2.05-2.16 (m, 1H), 2.16 (s, Me), 2.16-2.30 (m, 2H), 2.38-2.47 (m, H—C(2)), 2.49-2.57 (m, H—C(1)), 5.60 (dd, J=8.2, 18.5, H—C(3)), 5.73 (dd, J=8.0, 18.3, H—C(4)). $^{13}$C-NMR (100 MHz, CDCl$_3$): δ24.19 (t, C(7)), 25.58 (t, C(5)), 26.13 (t, C(2)), 27.12 (t, C(8)), 28.08 (q, Me), 28.96 (t, C(6)), 52.66 (d, C(1)), 127.38 (d, C(3)), 131.48 (d, C(4)), 211.20 (s, CO). MS (EI): 152 (15), 137 (7), 134 (15), 119 (10), 109 (35), 94 (21), 79 (36), 67 (100), 55 (37), 43 (100). IR: ν$_{max}$ 3016, 2927, 2855, 1708, 1666, 1466, 1467, 1352, 1241, 1165, 1120, 959, 755, 706 cm$^{-1}$.

Odour description: agrestic, armoise, wormwood, thujone, natural.

EXAMPLE 2

1-cyclooct-3-enylpropan-1-one

Obtained according to the experimental procedure of Example 1 from cyclooctene (150 g, 1.36 mol), propionic anhydride (354 g, 2.72 mol) and zinc bromide (30.6 g, 0.14 mol) in 27% yield. Boiling point 60° C./80 mbar.

$^1$H-NMR (400 MHz, CDCl$_3$): δ1.04 (t, J=7.3, Me), 1.40-1.80 (m, 6H), 2.03-2.12 (m, 1H), 2.17-2.27 (m, 2H), 2.39-2.58 (m, H—C(2), CH$_2$CO, H—C(1)), 5.60 (dd, J=8.1, 18.5, H—C(3)), 5.73 (dd, J=8.4, 18.4, H—C(4)). MS (EI): 166 (18), 137 (16), 109 (41), 94 (19), 79 (25), 67 (100), 57 (83), 41 (34), 29 (39). IR: ν$_{max}$ 3017, 2928, 2855, 1708, 1669, 1464, 1413, 1375, 1115, 973, 754, 705 cm$^{-1}$.

Odour description: fruity, banana, tagete.

EXAMPLE 3

1-cyclooct-3-enyl-2-methylpropan-1-one

Obtained according to the synthetic procedure of Example 1 from cyclooctene (150 g, 1.36 mol), isobutyric anhydride (430.3 g, 2.72 mol) and zinc bromide (30.6 g, 0.14 mol) in 33% yield. Boiling point 85° C./80 mbar).

$^1$H-NMR (400 MHz, CDCl$_3$): δ1.08 (t, J=7.0, Me), 1.39-1.78 (m, 6H), 2.02-2.29 (m, 3H), 2.42 (dt, J=8.8, 13.6, H—C(2)), 2.62-2.70 (m, H—C(1)), 2.79 (h, J=6.9, H—C Me$_2$), 5.60 (dd, J=8.4, 18.4, H—C(3)), 5.74 (dd, J=8.0, 18.4, H—C(4)). MS (EI): 180 (17), 165 (1), 137 (21), 119 (6), 109 (59), 94 (9), 81 (13), 79 (14), 71 (32), 67 (100), 55 (29), 53 (10), 43 (63), 39 (20), 27 (14). IR: ν$_{max}$ 3017, 2967, 2928, 2857, 1701, 1666, 1466, 1382, 1051, 1004, 756, 735 cm$^{-1}$.

Odour description: fruity, green.

EXAMPLE 4

1-cyclooct-3-enylpropan-1-ol 1-cyclooct-3-enylpropan-1-one (84.0 g, 0.5 mol) was slowly added to a solution of sodium borohydride (11.9 g, 0.3 mol) in ethanol (330 ml) at 0° C. (ice bath), and stirring was continued at room temperature for 4 h. The reaction mixture was poured into ice-cold 2N HCl (500 ml) and extracted with MTBE (2×200 ml). After washing with brine (3×200 ml), drying (MgSO$_4$) and evaporation of solvents, the yellowish oily residue (86.6 g) was distilled over a 20 cm Widmer column (66-80° C./0.7-0.8 mbar) to give 69.2 g of 1-cyclooct-3-enylpropan-1-ol (colourless oil, 68% yield). It consisted of >90% of a 1:1 mixture of two diastereomeric racemates of 1-cyclooct-3-enylpropan-1-ol. An analytical sample was purified by flash chromatography (hexane/MTBE 3:1).

R$_f$ 0.51. $^1$H-NMR (200 MHz, CDCl$_3$): δ0.95 and 0.97 (2t, J=7.4 and 7.3, 3H), 1.22-1.76 (m, 10H), 2.02-2.27 (m, 4H), 3.32-3.46 (m, 1H), 5.54-5.70 (m, 2H). $^{13}$C-NMR: diast. rac. A: δ10.1 (q), 24.6 (t), 25.4 (t), 26.4 (t), 27.1 (t), 28.5 (t) 29.1 (t), 45.2 (d), 77.1 (d), 128.9 (d), 130.4 (d); diast. rac. B: δ10.2 (q), 24.2 (t), 25.3 (t), 26.8 (t), 26.9 (t), 27.8 (t), 28.9 (t), 45.2 (d), 77.1 (d), 128.9 (d), 130.3 (d). MS (EI): 168 (M$^+$,2), 150(16), 139(16), 121(76), 109(25), 107(26), 93(31), 82(28), 81(35), 79(49), 67(100), 59(50), 57(41), 55(43), 41(55). IR (neat): ν$_{max}$ 3359, 2925, 2856, 1466, 1106, 968, 755, 705 cm$^{-1}$.

Odour description: cassie, mimosa, green, moss, natural, forest, fatty

EXAMPLE 5

1-Cyclooct-4-enylethanone

A solution of 5-bromo-cyclooctene (5 g, 26 mmol; prepared by treatment of 1,5-cyclooctadiene with HBr in AcOH) in diethyl ether was added to magnesium (0.7 g, 29 mmol, 1.1 eq.). The resulting solution was cooled to 5° C. and treated dropwise with a solution of acetaldehyde (5 ml, 89 mmol, 3.4 eq.) in diethyl ether (10 ml). The resulting mixture was stirred 3 h at 20° C., treated with 2M HCl, and extracted with diethyl ether. The organic phases were washed successively with NaHCO$_3$, NH$_4$Cl and NaCl solutions, and dried (Na$_2$SO$_4$) and the solvent evaporated under vacuum. The crude product was purified by flash chromatography (hexane/Et$_2$O 10:1) to give 1.2 g of 1-cyclooct-4-enylethanone (30%).

$^{13}$C-NMR (100 MHz, CDCl$_3$): δ24.18 (t), 25.79 (t), 27.87 (q), 27.99 (t), 28.16 (t), 30.53 (t), 51.58 (d, C(1)), 129.65 (d), 130.53 (d), 212.28 (s). MS (EI): 152 (1), 137 (7), 134 (30), 119 (14), 109 (27), 105 (7), 94 (14), 79 (34), 67 (77), 55 (28), 43 (100), 39 (31).

Odour description: green leaves, thuja oil, armoise, fruity.

EXAMPLE 6

1-Cyclooct-2-enylethanol and 1-cyclooct-2-enylethanone

At −50° C., a solution of 3-bromo-cyclooctene (4.2 g, 22 mmol; prepared by reaction of cyclooctene with N-bromosuccinimide) and titanium(IV)isopropoxide (7.2 ml, 24 mmol, 1.1 eq.) in diethyl ether (100 ml) was treated with a 2M solution of isopropylmagnesium chloride in diethyl ether (49 mmol, 2.2 eq.). The resulting mixture was stirred 1.5 h at −50° C., treated with acetaldehyde (1 ml, 18 mmol, 0.8 eq.), stirred 1 h at −40° C., and treated with 2M aqueous HCl solution. After extraction with MTBE (2×100 ml), washing of the organic phases with water (2×200 ml) and aqueous NaCl solution (200 ml), and drying (MgSO$_4$), the crude product (4.4 g) was purified by flash chromatography (hexane/MTBE 6:1) to give 0.7 g of 1-cyclooct-2-enylethanol (26%).

$^{13}$C-NMR (100 MHz, CDCl$_3$): δ21.27 (q), 25.51 (t), 26.64 (t), 26.82 (t), 29.38 (t), 31.78 (t), 43.83 (d), 71.44 (d, CHOH), 130.43 (d), 130.54 (d). MS (EI): 154 (1), 136 (1), 121 (2), 110 (48), 95 (25), 82 (100), 67 (93), 54 (35), 45 (65), 41 (43).

Odour description: green, earthy, fruity, fresh

At 0° C., a solution of 1-cyclooct-2-enylethanol (1.4 g, 9 mmol) in dichloromethane (20 ml) was added to pyridiniumchlorochromate (2.35 g, 11 mmol) in dichloromethane (30 ml). The resulting mixture was stirred at 20° C. during 3.5 h and filtered through Celitee ®. The filtrate was concentrated and the crude product purified by flash chromatography (hexane/Et$_2$O 6:1) to give 0.7 g of 1-cyclooct-2-enylethanone (55%).

$^{13}$C-NMR (100 MHz, CDCl$_3$): δ25.20 (t), 26.41 (t), 26.58 (t), 28.73 (q), 29.14 (t), 31.77 (t), 50.38 (d), 127.40 (d), 131.83 (d), 210.52 (s, CO). MS (EI): 152 (14), 137 (4), 134 (5), 124 (3), 110 (4), 109 (31), 95 (18), 94 (10), 81 (20), 79 (21), 67 (98), 55 (29), 43 (100), 39 (22).

Odour description: green, thuja oil, wormwood, fruity.

EXAMPLE 7

1-Cyclooct-1-enylethanone

At 35° C., a solution of lithium acetylide-ethylene diamine (50 g, 0.49 mol) in THF (500 ml) was slowly treated (reaction temperature≦35° C.) with a solution of cyclooctanone (51.4 g, 0.41 mol) in THF (100 ml). The resulting mixture was stirred for 4 h at 20° C., 15 h at 45° C., cooled to 5° C., treated with aqueous sat. NH$_4$Cl solution (250 ml) and washed with 3M aqueous HCl. After extraction with Et$_2$O, the organic phases were washed with water, aqueous sat. Na$_2$CO$_3$ solution, dried (Na$_2$SO$_4$), and concentrated to give 1-ethynylcyclooctanol (66.6 g). A solution of crude 1-ethynylcyclooctanol (65 g) in formic acid (130 ml) was heated for 2.5 h at 80° C. The resulting mixture was taken up in Et$_2$O and washed successively with water, 5M NaOH, water, aqueous sat. NH$_4$Cl solution, dried (Na$_2$SO$_4$), and concentrated to give 56 g of crude product. A fraction (8 g) was purified by flash chromatography (hexane/Et$_2$O 95:5→9:1) to give 4.1 g of 1-cyclooct-2-enylethanone.

MS (EI): 152 (43), 137 (31), 123 (15), 109 (48), 81 (21), 67 (67), 55 (23), 43 (100).

Odour description: fruity, sweet, anisic, minty, terpineol, camphoraceous.

EXAMPLE 8

1-Cyclooctylpropanone

A solution of 1-cyclooct-3-enylpropan-1-one (1.5 g, 9 mmol) in ethanol (20 ml) was treated with 10% palladium on charcoal (0.09 g) at room temperature and the resulting suspension was hydrogenated during 40 min. at 20 bars. After filtration through Celitee ® and concentration under vacuum, the crude product was purified by flash chromatography (hexane/Et$_2$O 19:1) to give 0.78 g of 1-cyclooctylpropanone (52%).

$^{13}$C-NMR (100 MHz, CDCl$_3$): δ8.06 (q), 25.54 (t, 2 CH$_2$), 26.28 (t), 26.60 (t, 2 CH$_2$), 28.16 (t, 2 CH$_2$), 33.95 (t), 50.47 (d), 215.15 (s, CO). MS (EI): 168 (3), 139 (17), 111 (47), 69 (100), 55 (55), 41 (45), 29 (34).

Odour description: fruity, green.

EXAMPLE 9

1-Cyclooctylethanone

Obtained according to the synthetic procedure of Example 8 from of 1-cyclooct-3-enylethanone in 49% yield. Boiling point 154° C./120 mbar.

$^{13}$C-NMR (100 MHz, CDCl$_3$): δ25.47 (t, 2 CH$_2$), 26.24 (t), 26.60 (t, 2 CH$_2$), 27.94 (t, 2 CH$_2$), 28.01 (q), 51.54 (d). MS (El): 154 (4), 139 (3), 125 (6), 111 (18), 96 (19), 81 (10), 69 (100), 55 (58), 43 (66), 39 (19).

Odour description: agrestic, camphoraceous, armoise, thujone-like, earthy, woody.

EXAMPLE 10

1-Cyclooctyl-2-methylpropanone

A solution of 1-cyclooct-3-enyl-2-methylpropanone (5.0 g, 28 mmol) in ethanol (50 ml) was treated with 10% palladium on charcoal (0.2 g) at room temperature and the resulting suspension was hydrogenated during 60 min. at 20 bars. After filtration through Celitee ® and concentration under vacuum, the crude product was purified by flash chromatography (hexane/Et$_2$O 19:1) to give 0.9 g of 1-cyclooctyl-2-methylpropanone (43%).

$^{13}$C-NMR (100 MHz, CDCl$_3$): δ18.59 (q, 2 Me), 25.56 (t, 2 CH$_2$), 26.34 (t), 26.55 (t, 2 CH$_2$), 28.30 (t, 2 CH$_2$), 39.28 (d), 48.71 (d), 218.26 (s, CO). MS (El): 182 (5), 167 (1), 153 (1), 139 (16), 111 (66), 69 (100), 55 (41), 43 (39), 41 (39).

Odour description: floral, fruity, balsamic.

EXAMPLE 11

1-Cyclooctyl-2-methylpropanol

A suspension of sodium borohydride (0.29 g, 8 mmol) in methanol (30 ml) was treated with a solution of 1-cyclooctyl-2-methylpropanone (2.0 g, 11 mmol) in methanol (20 ml) at room temperature. The resulting mixture was stirred at 20° C. during 20 h, poured over 2 M aqueous HCl (50 ml) and extracted with MTBE (2×80 ml). The organic phases were washed with water (100 ml), aqueous sat. NaCl solution (100 ml), and dried (MgSO$_4$). The crude product was purified by flash chromatography (hexane/Et$_2$O 7:1) to give 1.7 g of 1-cyclooctyl-2-methylpropanol (81%).

$^{13}$C-NMR (100 MHz, CDCl$_3$): δ17.41 (q), 19.93 (q), 25.68 (t), 26.25 (t), 26.34 (t), 26.68 (t), 26.77 (t), 27.03 (t), 30.32 (d), 31.12 (t), 39.25 (d), 82.35 (d). MS (El): 183 (1), 166 (1), 141 (14), 123 (33), 110 (11), 95 (12), 81 (59), 73 (100), 69 (31), 55 (63), 41 (41).

Odour description: floral, woody, rosy, fruity.

EXAMPLE 12

A fragrance Composition for a Soap

| compound/ingredient | parts by weight 1/1000 |
|---|---|
| Civette GIVCO 208* | 1 |
| Ethyl vanilline | 1 |
| cis-Jasmone | 1 |
| Castoreum GIVCO 116* | 2 |
| Galbanum GIVCO 121* | 2 |
| Aldehyde C11 Undecylic | 3 |
| Cyclal C | 3 |
| Petitgrain essential oil Paraguay | 3 |
| Iso Butyl Quinoleine (at 10% in DPG) | 3 |
| Evernyl | 4 |
| Dimethyl Anthranilate | 4 |

-continued

| compound/ingredient | parts by weight 1/1000 |
|---|---|
| Givescone | 5 |
| Dimethyl Octenone | 6 |
| Labienoxime (1%/CQS) | 6 |
| Tangerinol | 6 |
| Sandalwood GIVCO 203* | 6 |
| Florhydral | 7 |
| Allyl Amyl Glycolate | 8 |
| Romarin essential oil | 8 |
| Velvione | 10 |
| Coumarin | 10 |
| Okoumal | 10 |
| Thibetolide | 10 |
| Oxyoctaline Formate | 15 |
| Isoraldeine 95 | 15 |
| Gaiacwood essential oil | 20 |
| Lemon essential oil California | 20 |
| Patchouli essential oil | 20 |
| Amyl Salicylate | 20 |
| Benzyl Acetate | 30 |
| Geranodyle | 35 |
| Citronellol | 40 |
| Lavandin Grosso essential oil | 50 |
| Alpha Hexyl Cinnamic Aldehyde | 80 |
| Dihydro Myrcenol | 130 |
| Bergamote GIVCO 104* | 200 |
| Dipropylene Glycol | 203 |
| Compound of formula I | 3 |
| | 1000 |

*Fragrance Ingredients Index 2002. Givaudan S. A.

A) Adding 1-cyclooct-3-enylethanone to the fragrance composition significantly increases the diffusion of the whole fragrance, offering a better base coverage of the soap. 1-cyclooct-3-enylethanone adds a sophisticated agrestic note in the range of armoise oil, with ozonic, cucumber undertones. It also imparts more volume to the woody accord.

B) Adding a mixture of 1-cyclooct-3-enylethanone, 1-cyclooct-3-enylethanone, and 1-cyclooct-3-enylethanone in the ratio of about 60:30:10 parts by weight to the fragrance composition imparts less sweet and more fresh, agrestic notes in the range of armoise oil/wormwood with similar strength and enhanced diffusivity compared to Example B.

The invention claimed is:

1. A fragrance composition comprising a mixture of
A) a compound of formula Ic

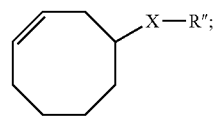

and

B) a compound of formula Ia, and a compound of formula Id

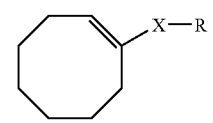

-continued

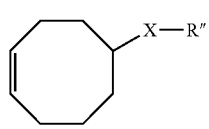

Id wherein X is carbonyl, or —(CHOH)—; and
R is methyl or ethyl, or linear or branched C3 to C5 alkyl;
or R is vinyl or linear or branched C3 to C5 alkenyl;
and R=R''=R''' and X=X''=X'''.

2. A fragrance application comprising the fragrance composition according to claim 1.

3. A fragrance application according to claim 2, wherein the fragrance application is selected from a perfume, household product, laundry product, body care product or cosmetic.

4. A method of manufacturing a fragrance application, comprising the step of incorporating the composition according to claim 1 into the fragrance application.

5. A method according to claim 4, wherein the fragrance application is selected from a perfume, household product, laundry product, body care product or cosmetic.

* * * * *

UNITED STATES PATENT AND TRADEMARK OFFICE
CERTIFICATE OF CORRECTION

PATENT NO. : 7,605,118 B2  Page 1 of 1
APPLICATION NO. : 10/531809
DATED : October 20, 2009
INVENTOR(S) : Granier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1167 days.

Signed and Sealed this

Fifth Day of October, 2010

David J. Kappos
*Director of the United States Patent and Trademark Office*